US008372820B2

(12) United States Patent
Litvin et al.

(10) Patent No.: US 8,372,820 B2
(45) Date of Patent: Feb. 12, 2013

(54) COMPOSITION COMPRISING SILICONE OIL OR OILS STRUCTURED WITH COMPOLYMERS CARRYING GREATER THAN 70% LONG CHAIN ALKYL GROUP

(75) Inventors: Tamara Litvin, Woodbridge, CT (US); Qiu Qiang, Trumbull, CT (US); Alexander Lips, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 478 days.

(21) Appl. No.: 12/423,987

(22) Filed: Apr. 15, 2009

(65) Prior Publication Data

US 2010/0266524 A1 Oct. 21, 2010

(51) Int. Cl.
*A61K 31/695* (2006.01)
*A61K 8/02* (2006.01)
*A61Q 5/12* (2006.01)

(52) U.S. Cl. .............. 514/63; 424/70.12; 424/70.15; 424/401

(58) Field of Classification Search .............. 424/401, 424/70.12, 70.15
See application file for complete search history.

(56) References Cited

U.S. PATENT DOCUMENTS

| | | | |
|---|---|---|---|
| 5,266,321 A | 11/1993 | Shukuzaki et al. | |
| 5,308,526 A | 5/1994 | Dias et al. | |
| 5,387,417 A | 2/1995 | Rentsch | |
| 5,494,657 A | 2/1996 | Swenson | |
| 5,558,872 A | 9/1996 | Jones et al. | |
| 5,622,793 A | 4/1997 | Tijima et al. | |
| 5,643,899 A | 7/1997 | Elias et al. | |
| 5,744,146 A | 4/1998 | Peters et al. | |
| 5,792,467 A | 8/1998 | Emerson et al. | |
| 5,849,314 A | 12/1998 | Dobkowski et al. | |
| 6,180,127 B1 * | 1/2001 | Calton et al. | 424/409 |
| 6,238,682 B1 | 5/2001 | Klofta et al. | |
| 6,264,963 B1 | 7/2001 | Leifheit et al. | |
| 6,524,562 B2 | 2/2003 | Guskey | |
| 6,555,099 B2 | 4/2003 | Guskey et al. | |
| 6,582,683 B2 | 6/2003 | Jezior | |
| 2004/0202624 A1 | 10/2004 | Pfluecker et al. | |
| 2005/0232881 A1 * | 10/2005 | Franklin | 424/66 |
| 2006/0165626 A1 | 7/2006 | Ricard et al. | |

FOREIGN PATENT DOCUMENTS

| | | |
|---|---|---|
| EP | 0 819 428 A2 | 1/1998 |
| FR | 2 931 068 A1 | 11/2009 |
| WO | 98/55086 A1 | 12/1998 |
| WO | 99/51192 A2 | 10/1999 |

OTHER PUBLICATIONS

Bockisch, M. Fats and Oils Handbook, 1998, AOCS Press, p. 506.*
PCT International Search Report and Written Opinion on Application No. PCT/EP2010/054832 dated Sep. 14, 2010.
"Sales Specification Ganex V-220" May 24, 2006. XP002593625 retrieved from the Internet: URL:www.ispcorp.com on Jul. 22, 2010.
Co-pending application for: Applicant: Litvin et al.; U.S. Appl. No. 12/423,984, filed Apr. 15, 2009, entitled: Petrolatum Based Composition Comprising Greater Than 10% Silicone for Improved Feel While Remaining Stable.

* cited by examiner

*Primary Examiner* — Gina C Justice
(74) *Attorney, Agent, or Firm* — Ronald A. Koatz (57) ABSTRACT

The present invention discloses silicone oils which are structured with a copolymer comprising a large percentage of alkane groups. Using high percentage pendant alkane helps provide silicone with ideal gel properties (G'>G", particularly >1000 cP, more preferably 2000-30,000 cP) and viscosity, after fracture, of 10 to 1000 cP, preferably 30-500 cP MW of polymer and exact chain length are selected to ensure that, when forming gel upon cooling after mixing polymer and silicone, the polymer viscosity will not be so high upon crystal formation that gel cannot form, yet also will not be so low that polymer will phase separate.

12 Claims, 3 Drawing Sheets

FIG. 1
MOLECULAR STRUCTURE OF GANEX V220 (PVP-EICOSANE COPOLYMER)

R=H OR Alkyl GROUP

COMPOSITION COMPRISING SILICONE OIL OR OILS STRUCTURED WITH COMPOLYMERS CARRYING GREATER THAN 70% LONG CHAIN ALKYL GROUP

FIELD OF THE INVENTION

The present invention relates to structured silicone oils. Such oils typically help provide excellent skin feel. Silicone oils are traditionally structured using silicone-based elastomers. The silicone oils of the present invention, by contrast, are structured with copolymer carrying large amount (e.g., greater than 70% of the structuring copolymer) of alkyl groups, preferably long chain ($C_{10}$-$C_{30}$, preferably $C_{18}$-$C_{24}$, more preferably $C_{20}$ to $C_{24}$) alkyls, especially α-olefins.

In a separate application, applicants claim specifically petrolatum compositions structured with silicone. In that application, the silicone is primarily structured with fatty acids. Although the copolymers with large percentage of long-chain pendant alkyl of the subject invention may optionally be used to further help structure the silicone in the compositions of the copending application, they are required and are the primary structurant in the structured silicone oils of the subject invention.

BACKGROUND

Silicone oils are widely used in the skin care and cosmetic industry. As noted, traditional silicone gel thickening systems (i.e., silicones which are themselves structured and can in turn be used to structure other benefit agents, such as petrolatum) typically use silicone based elastomers to structure the silicone oil. Formulation space in these systems is limited because, for example, addition of polar and non-polar benefit oils (e.g., to be delivered in compositions in which the structured silicone is used) may cause de-swelling of the silicone and/or phase separation.

Quite unpredictably, applicants have found that, if the silicone is instead structured with a unique gelling or structuring system (rather than traditional silicone gel thickener/gellants) comprising a semi-crystalline copolymer backbone having pendant side chains which form crystals to aid gelation, upon cooling (at temperature <35°, preferably <30° C.; melting point is above this, e.g., >35°-40° C.) and wherein >70%, preferably >75% of the pendant groups are alkane groups of certain minimum chain length grafted to a copolymer backbone, the silicone will provide the benefits of silicone (superior skin feel). At the same time these copolymers will more readily help deliver separate benefit actives (e.g., fatty acids such as stearic acid, petroselenic acid, oleic acid, linoleic acids; branched, saturated and unsaturated hydrocarbons such as squalane, squalene etc.) from a hydrocarbon phase which phase is formed by a combination of the copolymer grafted alkane chains (e.g., $C_{20}$ group grafted to polyvinylpyrrolidone, or PVP) and the type of low-molar mass hydrocarbons defined as benefit actives above. That is, the pendant groups on the copolymer and the separate benefit agents together form the "hydrocarbon phase". While not wishing to be found by theory, it is believed that thickening of the silicone is caused by formation of a gel network due to crystallization of the pendant alkyl chains (only the side chains crystallize while the backbone is amorphous).

The copolymer chain carrying the pendant alkyl groups may comprise, for example, (1) statistically random copolymer, graft-copolymers, or block copolymers; and (2) a cross-linked (network) copolymer which together form "backbone". Other hydrocarbons (e.g., fatty acids, long chain alcohols and paraffins) can be added to the copolymer (forming part of hydrocarbon phase as noted above) as they are miscible with the side chains of the copolymer. As indicated, the benefit agent actives (e.g., fatty acids and other skin actives), if used, preferably interact with pendant groups on the polymer and/or cross-linked (network) copolymer (backbone) to form part of the hydrocarbon phase (i.e. form crystals, mesomorphic structures, and or phase-separated domains and microdomains), and help structure the silicone oil. In this way, the pendant alkyl groups perform multiple tasks. They help "thicken" silicone and better deliver the superior feel silicone; and they interact with optional benefit agent, to help better deliver these.

The "silicone gelling system" of the invention thus comprises a combination of the silicone oil; backbone copolymers bearing alkyl chains; and optional hydrocarbons (i.e., hydrocarbons which can separately provide benefit). While not wishing to be bound by theory, it is believed that using copolymers which have high content of long chain alkyl helps make the silicone gel sensitive to shear, and provides a unique gel fracture rheological profile (gel fracture is point where crystalline network is broken and gel becomes more liquid-like) having minimal viscosity after the gel is destroyed on the skin. This unique gel fracture mechanism is beneficial both for skin feel and to help active release on deposition off the structured silicone. The gel is also characterized by the fact that it retains shape when subject to earth gravity (i.e., flip over 100 g container to observe liquid), even after five minutes. In addition, these gels are phase stable after three months.

The gel system is also temperature sensitive, i.e., may soften on the skin and melt. It can behave similar to petrolatum in this sense, but with improved sensory (silicone sensory) and controlled release (based on gel fracture Theological profile noted by using this gelling system). It should be noted that the gelling system can comprise just the copolymers plus silicone oil. Separate hydrocarbons are not necessary to form gel, but are used to deliver skin care benefits.

In short, the mechanism of silicone gel formation and resulting gel so formed are new because the gel (formed by silicone oil and copolymer) is stabilized by semi-crystalline copolymer that carries at least 70% by weight alkane having chain length of $C_{18}$-$C_{30}$, preferably $C_{20}$-$C_{24}$. The ideal chain length for gelation within the range is really dependent on the composition of pendant chains (e.g., total amount) and molecular weight of overall polymer. One can also have effective gelation for $C_{30}$, for example, provided that there are fewer pendant groups. However, since the melting temperature of alkyl chains increases very rapidly with their length, $C_{20}$ is preferred from the processing stand point. In short, amount and chain length of hydrocarbon chains need to be selected so the polymer is soluble enough to form a gel but not so soluble as to phase separate. As indicated, copolymer may comprise optional separate hydrocarbon.

In general, silicone oils are used in many patents (e.g., U.S. Pat. No. 6,555,099 to Guskey et al.; U.S. Pat. No. 6,524,562 to Guskey). Copolymers like those used as gellant in the subject invention (e.g., U.S. Pat. No. 5,622,793 to Iijima et al.; U.S. Pat. No. 6,582,683 to Jezior) are also disclosed, but it is unpredictable they could be used as silicone structurants or what effect they would have.

As far as applicants are aware, there is no reference disclosing the copolymers comprising these long chain alkyl groups of the subject invention used as gellants or structurants of silicone oil (e.g., silicone polymer comprising such polymers); or the benefits associated with use of such unique gellant system. Further, such structured silicones would not form spontaneously and the process would have to be designed to ensure such silicones are formed. Therefore, the fact that these polymers yield such gels is quite unpredictable.

BRIEF DESCRIPTION OF THE INVENTION

The present invention provides uniquely structured silicone oil compositions. Specifically, the invention comprises a structured silicone oil composition comprising:

(1) 60 to 99%, preferably 70 to 95% silicone oil; and
(2) 5 to 30%, preferably 7 to 20%, more preferably 9 to 11%, most preferably about 10% by wt. of a copolymer comprising:
  (a) greater than 70% by weight of copolymer comprising pendant alkane groups having chain length $C_{10}$ to $C_{30}$, preferably $C_{18}$ to $C_{30}$, more preferably $C_{20}$ to $C_{24}$, even more preferably about $>C_{20}$ to $C_{24}$ (typically, the long chain pendant groups are crystalline at room temperature and have a melting point, assuming 10% mixture of polymer in 90% silicone, of about $>35°$ to $40°$ C.; backbone does not crystallize and typically remains amorphous); and
  (b) 1 to less than 30% by weight of copolymer of a fatty acid, long chain alcohol or n-alkane backbone monomer capable of bearing pendant alkyl groups. Preferred include vinyl amide monomer (e.g., as backbone of copolymer to which pendant alkyl groups are attached), particularly cyclic vinyl amide monomer such as vinyl pyrrolidone or any other monomers that may form a polymer backbone and bear grafted alkyl chains; while PVP is a preferred co-monomer, other examples of copolymer structures are described below. It is important that the molecular weight of the copolymer must not be too low as to be too soluble and phase separate (e.g., MW>10,000, preferably >12,000, even more preferably >15,000. Molecular weight of a copolymer Ganex V220 used in examples is 17,400. Further increase of the molecular weight, e.g., should be below 25,000, preferably <25,000, may be undesirable as this might reduce the solubility of a copolymer and make it difficult to form gel) and that length of pendant alkyl chains (e.g., >70%, preferably >75% by wt. have chain length, $>C_{18}$-$C_{30}$, especially $>C_{18}$ to $C_{24}$) be sufficient to ensure crystallization/gelation (gelation referring to gelation of entire 5 system, i.e., copolymer and silicone, thus, for example, copolymer forms a space-spanning network with silicone oil inside). In one embodiment, for example, eicosane groups comprise about 80% by wt. of polymer. The thickening effect may be reduced if the fraction of eicosane groups is smaller; or if fraction is same, but shorter chain length alkyl groups are used (i.e., decreasing % of total alkyl); and
(3) Optionally 0 to 70%, preferably, 1 to 50%, more preferably 3 to 40% by wt. (with resulting reduction in silicone and/or polymers) of fatty acid and/or saturated and/or unsaturated hydrocarbon as noted above as benefit agent interacting with pendant alkyl groups to further stabilize gelling system.

The gel is further characterized (assuming MW of polymer and length and amounts of pendant groups are properly selected) in that, upon inversion of the gel to earth gravity, it will not visibly flow after five minutes; and that the gels are phase stable after three months. Further, because of the way this gel is formed with defined polymer, it has solid-like properties initially (defined by G'>G" and G'>300 Pa, preferably >500, more preferably >1,000 but at least high enough to ensure the gel is "stable" as defined below), but upon fracture (when used by consumer on skin), reduces to viscosity of 20-2000 cP.

In a second embodiment, the invention comprises compositions (e.g., liquid cleaners, shower gels) comprising these structured silicone oils. These compositions can be used in skin care formulas such as body and face care lotions and creams, shower gels, and hand creams.

The structured silicone oils, when used in a shower gel or shower cleansing composition, provide a unique gel fracture, i.e. sharp transition from semi-solid (gel state) to liquid state, with the elastic modulus (measure of viscosity at rest) decreasing from about $10^2$-$10^5$ Pa to 0.1-10 Pa; rheological benefits, and minimal viscosity which help provide skin feel (from silicone oil) along with active release and deposition. Example 2 shows the composition of silicon oil used with Petrolatum where petrolatum concentration is 60% by weight. Although the structured silicones of the invention can be used to enhance deposition of petrolatum when the silicone of composition is dispersed in petrolatum, the structured silicone is preferred for use with other benefit agents (e.g., fatty acids).

In a third embodiment of the invention, the invention comprises cosmetic compositions which comprise the structurant silicone compositions.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

BRIEF DESCRIPTION OF THE FIGURES

FIG. 2 is a graph of dependencies of viscoelastic moduli (G' and G") and oscillatory stress amplitude on strain amplitude, frequency measured at 1 rad/s. Specifically, the figure shows that polymer (Ganex®V220) when used in combination with silicone oil (DC704) form a true gel. Such a true gel is defined by the ability of structured material to retain shape for a very long time. Specifically, the gel shows no visible flow when inverted to earth gravity at room temperature for at least five minutes (in addition, the gels are phase stable for at least two months, preferably three months). For most materials, these attributes occur if G'>G" (where G' is initially at least as high as necessary to retain shape on inversion as noted above), and when there is a critical deformation when gel starts to flow. In FIG. 2, this deformation is around 1% strain amplitude, and there is a stress peak associated with the fracture of a gel. At this point, G' and G" also become lower. This is not the case for all gels, but we see it for silicone structured by the copolymer. The shear thinning of this gel is greater than that of petrolatum jelly. So, FIG. 2 shows that G'>G" (Storage modulus>loss modulus) and that the gel "fractures" (breaks apart) at relatively low strain amplitude (10%). The stress measured as a function of strain amplitude shows a fracture peak which is characteristic for solid-like materials. This is beneficial to spreadability of silicone because the structured silicone behaves like a gel in the container at rest (has structuring viscosity), but becomes less viscous after fracturing. It is completely unpredictable that the specific copolymers of the invention could or would attain these benefits when used to structure silicone.

FIG. 3 is a graph of transient flow diagram obtained at continuous shear rate sweep (up curve from 0 to 1000 s$^{-1}$; and down curve from 1000 s$^{-1}$ to 0). According to the test, the stress is measured during same time interval (e.g., 10 s) when the shear rate increases from 0 to 1000 s$^{-1}$ (up-curve) and at decreasing shear rate 1000 s$^{-1}$ to 0. The transient flow experiment (thixotropic loop) was performed by increasing shear rate from 0 to 1000 s$^{-1}$ over time period of 10 seconds for gels with the following differing concentrations of Ganex® V220: 9.95%, 11%, 12%, 15%; shear stress was recorded as a function of shear rate when the shear rate was increasing and decreasing with time. The figure shows that the gel (Example 1-squares) has a sharp stress peak on the upper curve and a linear dependence of the stress versus shear rate after fracture (down curve), and this is indicative of Newtonian fluid behavior. This data show again how the structured silicone is advantageous for spreadability of silicone gel system because of its initial "solid-like" structuring at rest, followed by lowered viscosity after fracture. The viscosity in our case is 0.3 Pa*s, or 300 cP (Viscosity of pure oil is ~40 cP). The upper limit of viscosity could be several thousand cP as long as noted that there is lowered viscosity after fracture. Typically, viscosity after fracture can range from 10 to 2000 cP, preferably 20 to 1000, even more preferably 40 to 500 cP.

DETAILED DESCRIPTION OF THE INVENTION

The invention relates to novel silicone oil compositions which comprise silicone oil which is structured by a copolymer in which the copolymer alkane side chains having a chain length of $C_{10}$ to $C_{30}$, preferably $C_{18}$ to $C_{24}$, more preferably $C_{20}$ to $C_{24}$ comprises >70% by wt. of the polymer to ensure crystallization/gelation (of the final structured silicone); and 1-30% by weight copolymer of a backbone (including backbone of any network, e.g., where linear backbone chains may be cross-linked) preferably comprising vinyl amide monomer, preferably cyclic vinyl amide monomer such as poly vinyl pyrrolidone (PVP) or any other copolymer capable of bearing alkyl side chains noted. Total polymer should also have MW that is high enough to ensure it is not to liquidy and phase separated from silicone; yet not so high that it does not solubilize to a gel (e.g., MW>5000 to about 25,000). Optionally, there is present 0 to 70%, preferably 1 to 50%, more preferably 3 to 40% by wt. benefit agent (e.g., fatty acid, long chain alcohols or petrolatum) which, in combination with pendant alkyl chains from the copolymer or cross-polymer backbone, form a hydrocarbon phase which helps facilitate delivery of separate benefit agent when a composition comprising structured silicone and the separate benefit agent is applied to skin or other substrate. The "hydrocarbon" phase can be defined by pendant alkyl groups alone or alkyl groups in combination with benefit agents.

Specifically, the structured silicone oil compositions of the invention comprise:

(1) 60 to 99% by wt., preferably 70 to 95% silicone oil; and
(2) 5 to 30% by wt., preferably 5 to 20% by wt., more preferably 9 to 11%, most preferably about 10% by wt. of a structuring copolymer (amount is dependent on overall polymer MW, exact amount and chain length of pendant, etc. but must provide gel which is "stable" and further is initially solid-like, yet of defined viscosity on fracture) for the silicone oil comprising:
 (a) >70% by wt. of copolymer comprising pendant alkane groups having chain length $C_{10}$-$C_{30}$ ($C_{10}$ is shortest chain length viable to achieve desired crystal structuring effect), preferably $C_{18}$ to $C_{30}$, most preferably $C_{20}$ to $C_{24}$ (preferably the pendant chains are crystalline at <35° C., preferably ≦30° C. and melting point is ≧35°, preferably >35 to 40° C.; the copolymer backbone is amorphous and the copolymer helps make the final structured silicone gel); and
 (b) 1 to <30% by wt. copolymer of a backbone monomer capable of bearing pendant alkyl groups. Preferred include vinyl amide monomer, particularly cyclic vinyl amide monomer (e.g., polyvinylpyrrolidone or PVP) or any other monomer which can form polymer backbone bearing grafted alkyl chains (it may also include backbone of any network polymer); it is also important that MW of copolymer be large enough, e.g., MW>5000, preferably >10,000, more preferably >12,000, more preferably >15,000 to ensure no phase separation from silicone oil and of course that length of pendant alkyl (>70%, preferably >75% of length >$C_{10}$ to $C_{30}$) is sufficient to ensure gelation (by gelation is meant a silicone gel wherein G'>G" and viscosity, after fracture, is in range of 20 cP to 2000, preferably 30 to 1000 cP); and
(3) optionally, 0 to 70%, preferably 1 to 50%, more preferably 3 to 40% by wt., of benefit agent selected from the group consisting of fatty acids, saturated hydrocarbons, unsaturated hydrocarbons (e.g., squalane, squalene, etc.) and mixtures thereof. The optional benefit agent interacts with pendant alkyl chains to form "hydrocarbon phase" of structured silicone. Even when no benefit agent is present, the alkyl chains form the "hydrocarbon phase" (e.g., an excellent gel is formed when, for example, Ganex® V220 pendant groups help form crystals that work as cross-links between copolymer backbone chain thus forming the gel).

It is also important that pendant $C_{10}$-$C_{30}$ alkyl groups have structured regularity (to enhance crystallinity). In absence of regularity, (i.e., if polymer is polydisperse), no crystallization takes place and required gel will not form.

The structured silicone is characterized by "stability" which is defined by the fact that gel shows no visible phase separation after two months, preferably three months and that upon inverting, a container will not visibly flow under weight of gravity measured at room temperature (20-25° C., preferably 21-24° C.) for at least five minutes. In addition to "stability", the gel has solid like initial viscosity (defined by G'>G" and G'>300 Pa, preferably >500 Pa, more preferably >1000, but at least large enough to ensure stability as defined above) yet, upon fracture (e.g., when rubbed on skin by consumer during wash) has viscosity of 20-1000 cP.

The structured silicone oil compositions thus have improved gel fracture and rheology properties (e.g., solid like structuring viscosity at rest, and lowest viscosity after fracture) compared to hydrocarbon based structured oils; and, when used in liquid shower gel and/or cleansing compositions, help provide dual benefit of sensory feel from silicone as well as being able to effectively deliver separate actives (e.g., fatty acids) which may be part of the structuring hydrocarbon phase.

Silicone Oil

Composition of the invention comprise 60-99%, preferably 70-95% silicone oil. Silicone oils, also known as polymerized siloxanes are silicon analogues of carbon based organic compounds which may form molecules based on silicon rather than carbon. Specifically, chains are formed from repeating silicon-oxygen atom (—Si—O—Si—O—Si—) or siloxane. Other atoms attach to the tetravalent silicone atoms, but not to the divalent oxygens which form instead part of the silicone backbone chain.

A typical silicone oil is polydimethyl siloxane where two methyl groups attach to the silicon atom to form $(H_3C)[SiO(CH_3)_2]_nSi(CH_3)$ where n defines the length of the chain (n is typically >4). The upper limit of n is defined by the desirable viscosity of the silicone oil and n may be 4 to 850, preferably 8 to 400. Phenyl groups may be attached instead of methyl and would form phenyltris(trimethylsiloxy) silane (one phenyl group), tetraphenyl-dimethyidisiloxane (4 phenyl groups), trimethyl pentaphenyl trisiloxane (5 phenyl groups). Alkyl groups generally, for example, or a combination of phenyl and other alkyl groups may be grafted to the silicone backbone. Silicone oils may be mixed together if necessary to achieve better sensory, spreadability, structuring and stability of cosmetic formulations.

Examples of silicone oils which are sold as commercial products include DC-704®, DC 556 and PH-1555 HRI cosmetic grade silicone fluids sold by Dow Corning. Preferred oils include DC 704 or DC 556.

Copolymer

The silicone oil of the invention, rather than being structured by silicone elastomers, is structured by a copolymer which in turn is characterized by the fact that the copolymer comprises >70 by wt. of the polymer, e.g., >70 to 99%, preferably >75 to 99% by wt. of the polymer, pendant alkane groups having chain length $C_{10}$ to $C_{30}$, preferably $C_{18}$ to $C_{24}$, more preferably $C_{20}$ to $C_{24}$; and 1 to 30% by wt. of the polymer, of a backbone monomer, e.g., preferably a vinyl amide monomer, capable of bearing pendant groups. There may also be backbone network optionally bearing pendant groups which count towards the >70%.

The pendant alkyl groups should preferably have regularity. In the absence of such regularity (molecule is instead polydisperse), crystallization may not occur and desired structuring gel not form.

By regularity is meant that the branches (or side chains) attached to the main backbone chain(s) are, on average, all substantially the same length (±4 carbons, for example). This permits the chains to pack more readily and significantly enhance crystallization process.

Figure 1:
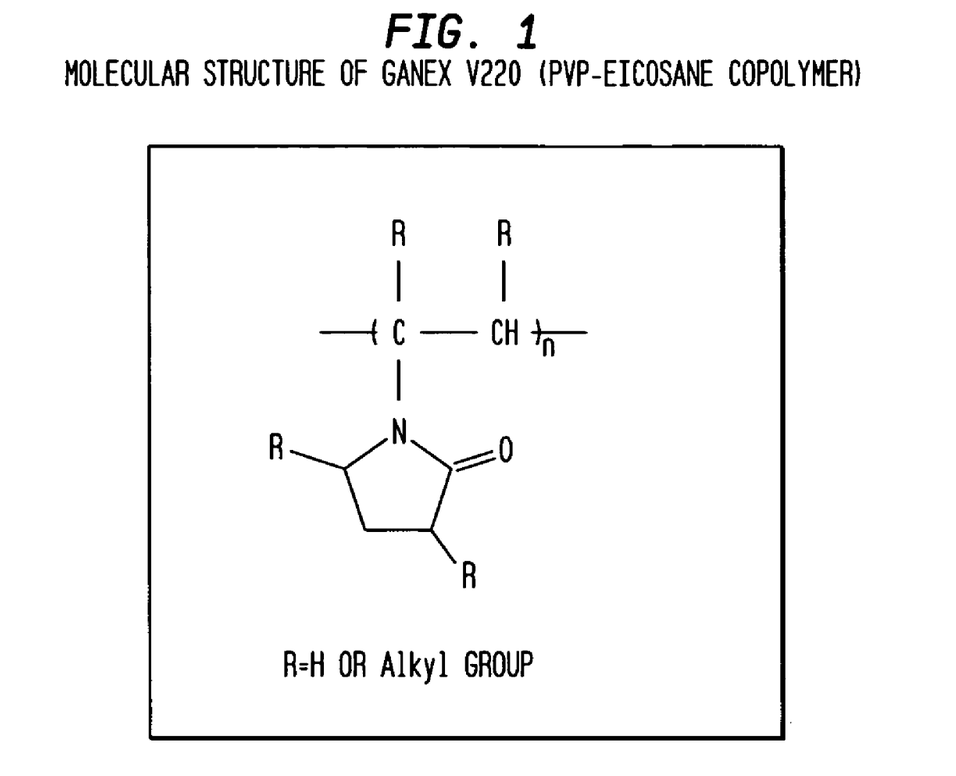
FIG. 1 is one example of the type of copolymer (e.g., polyvinylpyrrolidone-eicosane copolymer) which can be used in the novel silicone composition of the invention. The long chain pendant chains provide gel structure which is stable (to gravity when inverted) and solid-like, yet which is nicely spreadable upon fracture.
Figure 2:
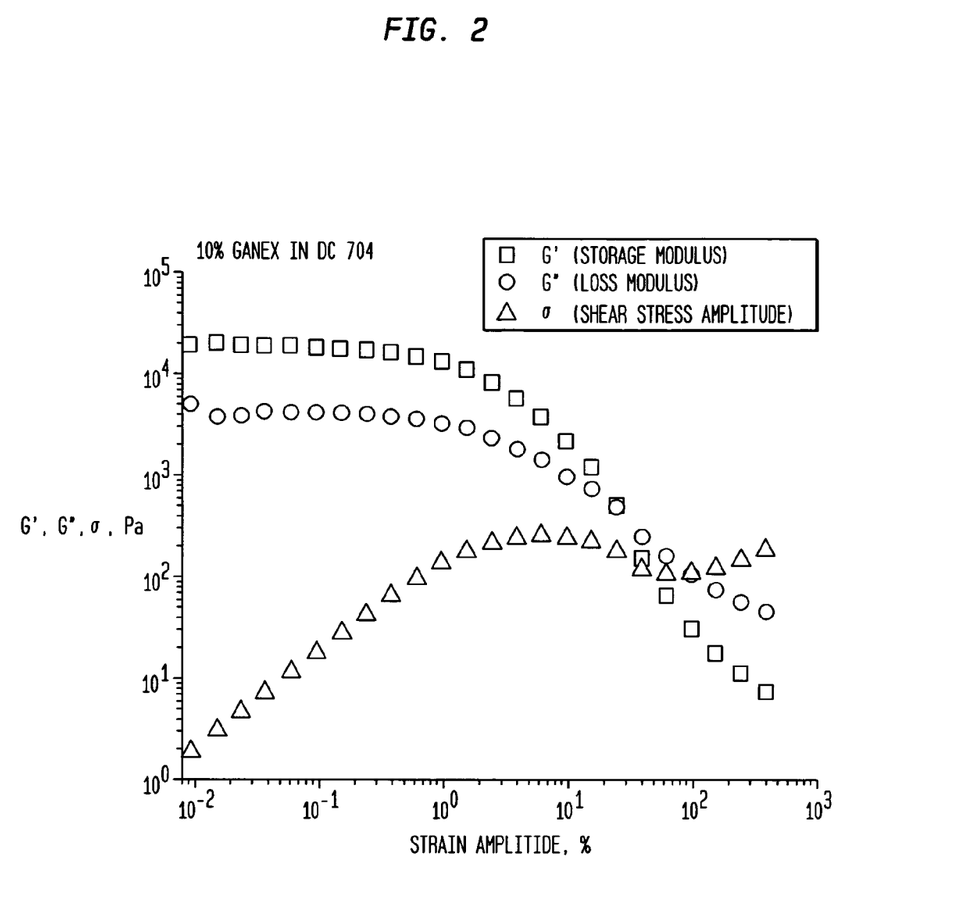
Figure 3:
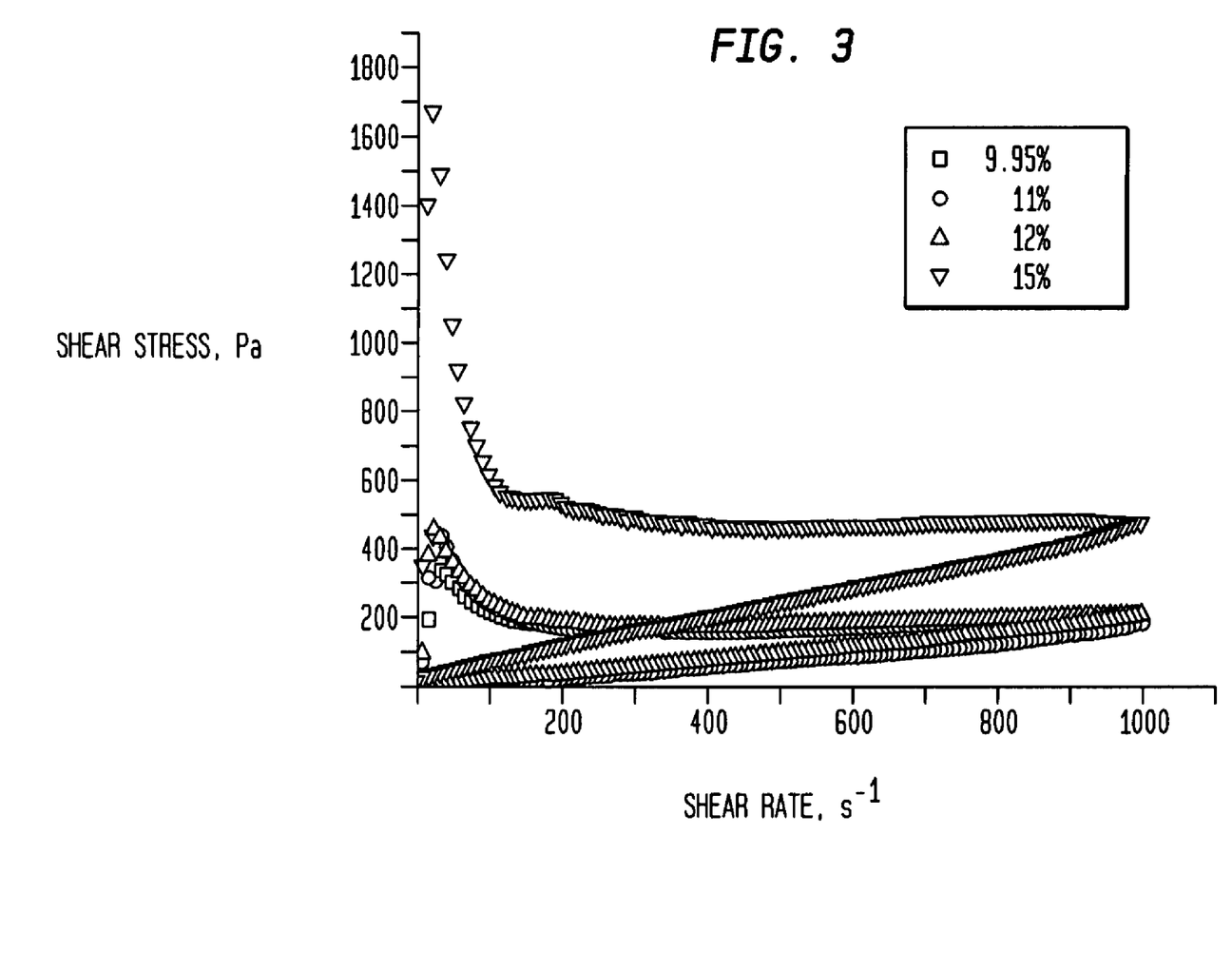

The copolymer itself may comprise 5-30% by wt., preferably 7-20% by wt., more preferably 9-11% by wt. (ideally about 10%) of the silicone/copolymer composition. The 9-11% range is preferred because this is the ideal range of onset of gelation (upon cooling) for copolymers which have predominantly (about 80%) $C_{20}$-$C_{24}$ chain length. Gelation is when standing viscosity and the elastic modulus would be expected to increase (i.e., when G'>G"). Below the gelation point, G' is a very close to zero, so that G'<<G". At gelation, the value of G' increases by several orders of magnitude, typically, from 0.1 Pa to several hundreds Pa. The gel in example 1, for example, has a very high modulus, i.e., 20,000 Pa. When the gel breaks (fracture point), the elastic modulus decreases down to 10 Pa (FIG. 2). As noted, the length of the average pendant chain and specific backbone monomer can also affect the onset of gelation. These variable are accounted for by defining a melting temperature of the pendant chains whereby pendant chains are crystalline at <35° C., preferably $\leqq$30° and melting point is $\geqq$35° C., preferably >35 to 40° C.

The copolymer itself, as noted, comprises greater than 70% by wt. pendant alkyl group which group must have chain length of $C_{10}$ to $C_{30}$. Since hydrocarbon melting temperature of crystalline pendant groups depends on chain length (i.e., the longer the chain length, the longer they will stay crystalline and enhance gelation), another way to define pendant groups is that, using a 10% copolymer mixture in 90% silicone oil as a standard, the pendant groups have a melting range of >30° C., preferably >35° C. and broad range of >30 to 45° C.; at the appropriate temperature (low enough to remain crystalline), the overall copolymer is believed semi-crystalline, with crystalline phase formed mostly by pendant chains and amorphous phase comprising mostly, for example, vinyl groups of backbone. Due to statistical variations of copolymers, there is some mixing of different types of groups.

The copolymer should also have MW of at least about 5000, preferably at least 10,000, e.g., 10,000-25,000 to ensure gelation. This is difficult to define precisely since it depends on concentration (1-30% by wt.). If composition is used in the highest range, MW could be lower range of 5-10%.

The pendant alkyl groups comprise singly bonded carbonated hydrogen groups. The alkyl groups must be long enough to crystallize, whether or not in silicone, so $C_{10}$ is the shortest viable chain length. Preferred alkyl groups are $C_{10}$ to $C_{30}$, preferably $C_{18}$ to $C_{24}$, more preferably about $C_{20}$ to $C_{24}$. A preferred alkyl group is $C_{20}$ eicosyl group. The copolymer is obtained by substituting the hydrogen atoms with $C_{20}H_{41}$— chains. There are 4 positions possible for such a substitution within the monomeric group. The preferred $C_{12}$ to $C_{30}$ alkyl groups typically will branch off the backbone, which backbone comprises a mixture of different chain alkyl groups and the vinyl amide monomer noted.

It should be noted that "onset of gelation" refers to minimum concentration (e.g., 90% silicone and 10% copolymer) of copolymer necessary to form gel. It is not desirable to use more copolymer if, for example, 10% is enough. If too much copolymer is used, the gel may be too stiff (e.g., may not have desirable spreadability in use). In general the ideal gel will have G'>G" (of course, the higher the value of G', the greater the suspension ability) and viscosity, after "fracture" of 10 cP to 7000 cP, preferably 30 to 1000, more preferably 30 to 500 and more preferably 30 to 250 cP. Viscosity, after fracture, is lower than G'. Typically, G' is >1000 cP, preferably 2000 to 30,000 cP, more preferably 2000 to 15,000 cP.

As for the repeating backbone monomer, this is typically a vinyl amide monomer, preferably a cyclic vinyl amide polymer such as vinyl pyrrolidone. The vinyl pyrrolidone backbone monomer (not just a monomer; Ganex® has alkyl chain grafted directly onto the PVP chain, such that the chain is more or less "coated" with "hairy" hydrocarbons, e.g., one monomer unit can carry up to four pendant hydrocarbon chains) typically comprises 1 to 30% by wt. of the entire copolymer.

The backbone, however, need not necessarily be vinyl amide and can be made of any monomers or co-monomers, including hydrophobically modified silicone polymers, polyacrylates, polymethacrylates. It may also comprise network polymers which may themselves optionally comprise pendant groups.

Examples of possible polymer structures are set forth below:
Possible Polymer Structures
C12-22 Alkyl Acrylate/Hydroxyethylacrylate Copolymer
C8-22 Alkyl Acrylate/Butyl Dimethicone Methacrylate Copolymer
Stearoxymethicone/Dimethicone Copolymer Steareth-10 Allyl Ether/Acrylates Copolymer
Poly C10-30 Alkyl Acrylate (IPA-13-6)
C8-22 Alkyl Acrylates/Methacrylic Acid Crosspolymer
Optional Benefit Agent The silicone oil containing copolymer described above may optionally contain 0 to 70%, preferably 1 to 50%, more preferably 3 to 40% by wt. (e.g., 70% petrolatum can be used) of benefit agent components which, in addition to the pendant alkyl groups, help form the "hydrocarbon phase" of the silicone.

Of course if "benefit agent" comprises >50% of structured silicone, this is effectively like structured silicone in benefit agent solution.

In general, the benefit agent may comprise fatty acids. These include $C_8$ to $C_{30}$ saturated and/or unsaturated acids such as, for example, stearic, petroselenic, oleic, linoleic, etc. It is possible to prepare mixtures of linear saturated hydrocarbon with unsaturated or branched fatty acids if needed. Although branches and unsaturated fatty acids may reduce melting temperature, the effect can be compensated for by increasing the length of grafted alkyl chains. If benefit agent is added, for instance fatty acids, they may form separate crystals with melting point not too far from, for example, Ganex® V200. Unsaturated fatty acids may reduce melting point (which is undesirable to the extent we want to maintain crystals to help gelation). In such cases, one can use higher melting point copolymer, for example, Ganex® WP-660.

The benefit agent may further comprise saturated and/or unsaturated hydrocarbon (other than fatty acids) such as squalane, squalene, structured and non-structured vegetable oils, fatty alcohols, etc.

The structured silicone may thus be used to help deliver separate benefit agent to skin or the substrate.

This invention comprises structuring silicone oil with these alkyl-chain copolymers, optionally with benefit agent. The benefit agent may be part of larger composition as described in co-pending application filed same date. The polymers have been used for non-silicone oil formulations, but it is unpredictable that, if used in silicone, they would behave in the ways we have found (e.g., provide gel properties defined). The properties of this novel material are different, especially the comparison with existing structured oils such as Petrolatum. For example, the silicones have shear thinning as shown by properties before and after gel fracture and wherein fracture occurs at low shear rates. No such fracture at low shear rates exists for petrolatum.

In a second embodiment, the invention comprises compositions (e.g., face care lotion and creams, such as hand creams, shower gels, hand creams etc.) which comprise the structured oil.

When used in such compositions, the oils may provide a unique gel fracture, specifically a sharp transition of the entire composition in which the structured oil is used from semi-solid to liquid state with elastic modulus decreasing from about $10^2$-$10^5$ Pascal (Pa) to 0.1-10 Pa (less viscous) when the gel is deformed (the gel is subjected to deformation in various flow regimes such as steady flow or oscillatory dynamic deformation regime). The structured silicone further provide rheological benefit and minimal viscosity which helps provide dual benefit of skin feel along with active release. Such fracturing (associated with spreadability) is ideally seen, for example, in composition comprising 90% silicone and 10% copolymer (e.g., Ganex®).

In another embodiment of the invention, the invention is directed to a process for obtaining silicone gel which has initial properties of solid (and G' is significantly high, typically, at least >300 Pa and at least high enough to ensure "stability" as defined) but which fracture to obtain spreadability (defined by viscosity range after fracture of 20-1000 cP) wherein such process comprises mixing 60 to 90% silicone oil as structuring copolymer comprising component (1), (2) and optionally (3) as defined above.

According to this process, the ingredients are heated (to 60-70° C.) and mixed and then cooled to room temperature to form gel.

In another embodiment of the invention, the structured silicone oil compositions of the invention may be formulated into aqueous or anhydrous cosmetic compositions (e.g., body or facial care compositions) containing the structured oil compositions, e.g., as part of the hydrophobic or fatty phase.

For example, most cosmetic preparations contain, at varying levels of concentration, a hydrophobic or fatty phase comprising a mixture of oil, a fat and/or wax. This is true, for example, for oil-in-water or water-in-oil emulsions, gels, oils for face and body care, milks and make-up products such as rouge or lipstick.

The structured oil composition of the present invention may comprise 1 to 80%, for example of the total weight of the cosmetic composition. In the case of oil-in-water emulsion or body care compositions, the structured oil composition will more typically comprise 1 to 30%, preferably 2 to 15%, more preferably 2 to 10% by wt. of the cosmetic composition. Typically, water will comprise 70 to 99% by wt. preferably 80 to 90% of such compositions.

As compositions have less and less water, structured oil composition may reach from 50 to 80% by wt. of the cosmetic. In a typical facial care application, they would comprise 40 to 70% by wt., preferably 45 to 65% by wt. of the cosmetic composition.

Other components which can be used in the hydrophobic or fatty phase of a cosmetic composition are vegetable or animal oils, synthetic oils, fats and/or wax.

Among vegetable or animal oils which may be used include almond oil, avocado oil, olive oil, jujube oil, jojoba oil, sesame oil, soybean oil, colza oil, squalene, lanolin and derivatives of any of the above.

Among synthetic oils may be used are ethyl and isopropyl palmitate, alkyl myristates (isopropyl, butyl or cetyl myristate), triglycerides of octanoic or decanoic acid, cetyl ricinoleate, stearyl octanoate, hydrogenated polyisobutene, etc.

Among waxes which may be used are included carnauba wax, beeswax, ozokerite, candelilla wax, Montan wax and microcrystalline waxes.

The hydrophobic phase can also contain small amounts of fatty alcohol (e.g., typically 0.1-3% by wt., preferably 0.2-1% by wt.). These include long chain alcohols such as cetylic alcohol, stearylic alcohol, myristic alcohol, hydrostearylic alcohol, oleic alcohol and the like. In addition, the fatty phase may contain certain polymers, for example, polyvinylpyrrolidone, typically in about 0.1-0.5% by wt.

As indicated, total amount of hydrophobic phase, including structured oil composition, varies depending on whether cosmetic composition is mostly aqueous, somewhat aqueous or non-aqueous and may vary typically from 3 to 99% by wt. of the cosmetic compositions.

As noted, cosmetic compositions may be all aqueous or anhydrous. The compositions may be fluid emulsions, lotions or more substantial emulsions. They may be, for example, milks or softening creams, milk or creams for hand care, makeup removing creams or milks, foundation bases, sunscreen milks or creams, artificial tanning milks or creams, milks or creams against perspiration, shaving creams or foams.

In one form, the compositions may comprise primarily (>50%, preferably >55% by wt.) hydrophobic phase, of which 80%-100% of said hydrophobic phase is structured oil composition, and which take the form of a sunscreen oil (containing, for example, 0.1-3%, preferably 0.5-2% of a sunscreen which absorbs ultraviolet rays), a hair care oil, a body or hair care oil, a pre-shave or after shave oil, a bath oil, a gel, an ointment or a stick.

When in the form of cream or milk, the cosmetic composition is typically in the form of water-in-oil or oil-in-water emulsion wherein hydrophobic or fatty phase (including predominantly, 80-100% structured oil composition) comprises 4 to 60% by wt., the water comprises 30 to 90% by wt. and an emulsifying agent comprise 0.5 to 20%, preferably 1 to 12% by wt. of cosmetic emulsion.

Among emulsifying agents non-limiting examples which may be used are as follows:

Fatty polyoxyethylene or polyglycerol alcohols, oxyethylene or non-oxyethylene alkyl sulfates, mixtures of at least one lanoate (e.g., magnesium, calcium, lithium, zinc or aluminum lanoate and hydrogenated lanoline and/or lanoline alcohol, esters of fatty acids and polyols such as glycerol or propylene glycol). Glycerol and propylene glycol are also functioning, for example, as humectants. Also can be used monoesters of fatty acids and polyoxyethylene sorbitan.

Cosmetic compositions may also include thickening agents and gellifying agents. These include, for example, magnesium and aluminum silicates; ether-vinylic/anhydride maleic copolymers (e.g., polymer sold as "Viscofas"®); carboxyvinylic polymers such as those sold under the name Carbopol®; or gels of organically modified montmorillonite and neutral oil such as for example the product Miglyol gel®.

In addition, the cosmetic composition may comprise various other components, typically at levels of 0.1-3% by wt. including coloring agents, perfumes, preserving agents, chelators, UV filters, pigments, pearlizing agents, mineral or organic fillers and vitamins.

Protocol

Rheological measurements were carried out using plate-plate geometry, strain-controlled instrument, in the dynamic regime, using oscillatory strain sweep and frequency sweep regimes, as well as transient flow regimes, such as thixotropic loop experiments. The strain sweep experiment is performed at constant frequency, typically at 1 rad/s while the amplitude deformation increases from 0.01% to 500%. At low deformations, the gel system behaves as a solid, which is specific for the system described in this invention (Example 1). The dependence of the shear stress amplitude from the strain amplitude remains linear before the gel breaks as a solid, with typical maximum at the fracture point. The transient flow experiment (thixotropic loop) was performed by increasing shear rate from 0 to 1000 $s^{-1}$ over time period 30s; the shear stress was recorded as a function of shear rate when the shear rate was increasing and decreasing with time. The gel system (Example 1) shows a fracture peak on the upper peak and the linear dependence of the stress vs. shear rate after fracture indicating Newtonian fluid behavior.

EXAMPLES

Example 1

Preparation of Structured Silicone Oil 90 g of silicone oil, tetramethyl tetraphenyl trisiloxane (trade name DC 704) was mixed with 10 g copolymer of polyvinylpyrrolidone (PVP) and eicosane, Ganex® V220 (that contains 80 wt % of eicosane), and heated above 60-70° C. to ensure complete melting of the copolymer. The liquid composition was vigorously mixed in the molten state using an orbital mixer. Then the composition was cooled to ambient temperature or below solidification temperature to form gel.

Example 2

Preparation of Silicone Oil with Copolymer Plus Added Benefit Agent 30.2 g of silicone oil, tetramethyl tetraphenyl trisiloxane (trade name DC 704) was mixed with 0.86 g palmitic acid, 0.44 g stearic acid, and 1.81 g lauric acid. 66.6 g of Petrolatum Jelly Snow White® was mixed with 0.09 g of copolymer Ganex® V220. All ingredients were heated above 60° C. to ensure complete melting of crystals. The liquid composition was vigorously mixed in the molten state using an orbital mixer. Then the composition was cooled to ambient temperature or below the solidification temperature.

The silicone oil is structured with Ganex® polymer and, in particular, pendant groups of the copolymer in combination with benefit agents (i.e., fatty acids) form hydrophobic phase. The melting point (above which pendant chains are no longer crystalline; only pendant groups can crystallize; PVP itself is non-crystalline polymer, however it has a softening point above 120° C. in the dry form) of >35° C. referred to earlier, refers to pendant chains; while 60° C. refers to entire copolymer within silicone oil. The decreasing elastic modulus (characteristic of Newtonian fluid system) refers to whole system.

Example 3

Preparation of Silicone Oil with Copolymer Plus Added Benefit Agent 70 g of silicone oil, tetramethyl tetraphenyl trisiloxane (trade name DC 704) was mixed with 10 g palmitic acid, 10 g stearic acid, 9.9 g lauric acid and 0.1 g of copolymer Ganex® V220. All ingredients were heated above 60° C. to ensure complete melting of crystals. The liquid composition was vigorously mixed in the molten state using an orbital mixer. Then the composition was cooled to ambient temperature or below the solidification temperature. Again, melting point of 60° C. refers to copolymer within silicone and decreasing elastic modulus refers to whole system.

Comparative Example A

Viscosity Criticality to Stability

10% of Ganex® V-216 (viscous liquid, 20% vinylpyrrolidone (VP), 80% C16 alfa-olefin, Melting Pt.=8.5° C.) mixed with 90% DC-704; results in low viscosity white liquid.

This is comparative example using VP-$C_{16}$ copolymer rather than VP-$C_{20}$. The VP-$C_{20}$ copolymer is wax. Specifically, VP-$C_{20}$ composition (in silicone) forms soft-solid gel at rest, and, when it breaks, has viscosity about 300 cP. VP-$C_{16}$, when added to silicone, forms fluid with viscosity lower than 300 cPs (i.e., not a gel). It is not certain if VP-C16 will lower the viscosity in the fluid state (i.e., this is not "stable" by inverted to gravity test). However, the viscosity is already very low viscosity, and it does not matter if it is 100 or 300 cP (for fracture). In general the viscosity depends on the polymer composition and architecture in a complex way so that the decrease of the grafted chain length does not always necessarily reduce the viscosity. Pure silicone (DC®-704), it is noted, has viscosity of only 39 cPs.

Comparative Example B

Chain Length Criticality

10% of Ganex® P-904 (white powder, 90% VP, 10% $C_4$ alfa-olefin, Melting Pt.=155° C.) mixed with 90% silicone (DC-704®). There was no solubility. Here polymer is VP-$C_4$ polymer is far below the VP-$C_{20}$ polymer of the invention. When chain lengths are shorter, the copolymer and silicone are substantially insoluble and the initial soft gel followed by fracture to good spreadability simply cannot be achieved.

Comparative C

MW Criticality

10% of Ganex® WP-660 (flaked solid, 20% VP, 80% $C_{30}$ alfa-olefin, Melting Pt.=63° C.) mixed with 90% silicone (DC-704®). Here, the mixture was microscopically phase separated into mixture of small gel particles in a fluid. Specifically, the molecular weight of Ganex WP-660 is much lower than that for Ganex V-220. It is believed to be in the low thousands, but it is definitely lower than 10,000. Therefore, the gel network is not forming if we add 10% of this polymer. Thus, at same concentration of polymer, the MW is important.

Comparative D

Criticality of Regularity

10% of Intelimer® IPA 13-6 (INCI Name Poly $C_{10}$-$C_{30}$ alkyl acrylate, Melting Pt.=65° C.)—no gel formed. The polydispersity of pendant chains can prevent crystallization of these chains. We believe that the crystalline regions formed by the pendant chains that belong to different backbone may create a continuous space-spanning gel network. The polydisperse chains of IPA 13-6 do not crystallize as easily as the monodisperse chains of Ganex V-220. Even if they do crystallize, the temperature of crystallization may be lower than the room temperature, therefore the gel is not formed. The gel may form at higher concentrations, though the gel will probably easily phase separate.

Comparative E

10% of Intelimer® IPA 13-1 (INCI Name Poly $C_{10}$-$C_{30}$ alkyl acrylate, Melting Pt.=48° C.)—no gel formed (no gel formed at tested concentrations) Negative examples with IPA-6 and IPA-1 demonstrate that side chains with big difference in number of C on side chain (polydisperse) do not form a gel.

Comparatives D and E demonstrate that side chain with big difference in number of C in side chain (polydisperse) do not form gel.

In general, the examples (e.g., Examples 1-3 Ganex® V220 using $C_{20}$-$C_{30}$ PVP-copolymer versus others with PVP $C_4$ or $C_{16}$ copolymer of Comparatives A and B or $C_{10}$ or $C_{30}$ number of carbons in Comparatives D and E) show that chain length on polymer should be at least about $C_{20}$ and have regularity of chain length to ensure formation of gel.

Comparative F

10% Ganex® V-516 (50% VP, 50% $C_{16}$, Tg=150° C., supplied as 55% actives in isopropanol which was stripped under vacuum 700 mm Hg at room temperature overnight) mixed with 90% silicone (DC-704®) dissolves in silicone and does not form gel. Upon cooling no gel was formed and the mixture was quite transparent indication that no crystals were formed. This example clearly shows there must be enough branching to form desired gel.

Example 4 and 5

In order to demonstrate the utility of the structured silicone compositions, the following compositions for body care (A) and facial care (B) were prepared.

A)

| Ingredient | % by Weight |
| --- | --- |
| Structured silicone* | 5 |
| Polymer | 0.2 |
| Alcohol | 0.73 |
| Emulsifier | 0.75 |
| Sunscreen | 1.25 |
| TiO$_2$ | 0.2 |
| EDTA | 0.04 |
| Humectant | 1.00 |
| Preservative | 0.2 |
| Vitamin | 1.25 |
| Water | Balance |

Structured silicone*: Copolymer (Ganex V-220) - 0.55%, DC-704 - 4.45%

B)

| Ingredient | % by Weight |
| --- | --- |
| Structured silicone** | 57 |
| Polymer | 0.2 |
| Alcohol | 0.73 |
| Emulsifier | 0.75 |
| Sunscreen | 1.25 |
| TiO$_2$ | 0.2 |

| Ingredient | % by Weight |
|---|---|
| EDTA | 0.04 |
| Humectant | 1.00 |
| Preservative | 0.2 |
| Vitamin | 1.25 |
| Water | Balance |

Structured silicone**: Copolymer (Ganex V-220) - 6.27%, DC-704 - 50.73%

The invention claimed is:

1. A structured silicone gel composition consisting essentially of:
   (a) 60 to 95% by wt. silicone oil; and
   (b) 5 to 30% of a structuring copolymer comprising:
      (1) greater than 70% by wt. of copolymer comprising pendant alkyl groups having chain length $C_{10}$-$C_{30}$; and wherein pendant chains are crystalline at <35° C., assuming mixture of 10% polymer and 90% silicone;
      (2) 1 to less than 30% by wt. of copolymer of a backbone monomer (including network cross-polymer, if any) capable of bearing said pendant alkyl group; and
   (c) optional 0 to 35% by wt. benefit agents,
wherein copolymer molecular wt. of greater than 10,000;
wherein structuring copolymer provides silicone gel (when cooled during formation) defined by having G'>G" and G' of at least 300 Pa and; viscosity after fracture of 10-2000 cP and wherein the cooled gel is further defined by ability to keep shape defined by the fact that upon inversion to gravity it will not visibly move for at least five minutes;
wherein said structured oil composition is made by mixing components (a), (b) and optional (c) in molten state and subsequently cooling to room temperature to solidify and form structured silicone gel.

2. A composition according to claim 1, wherein the structured silicone gel comprises 70 to 95% silicone oil and 5 to 20% copolymers.

3. A composition according to claim 1 wherein the copolymer used to form the structured silicone gel has MW 12,000 to 25,000.

4. A composition according to claim 1 wherein said backbone monomer forming part of structuring copolymer is a vinyl amide monomer.

5. A composition according to claim 4, wherein said vinyl amide monomer is cyclic.

6. A composition according to claim 5, wherein the structured silicone said vinyl amide polymer is vinyl pyrrolidone.

7. A composition according to claim 1 wherein said optional benefit agent is selected from the group consisting of $C_{20}$ to $C_{30}$ straight or branched, saturated or unsaturated fatty acids and saturated and/or unsaturated hydrocarbon (other than fatty acids).

8. A composition according to claim 7 wherein said fatty acid is selected from the group consisting of stearic acid, petroselenic acid, oleic acid, linoleic acid and mixtures thereof.

9. A composition according to claim 1 wherein, gel (after formation on cooling) has G" of >500 Pa.

10. A composition according to claim 1 wherein >70% pendant chain on the structuring copolymer have chain length $C_{18}$ to $C_{30}$.

11. A composition according to claim 10 wherein >70% pendant chain on the structuring copolymer have chain length $C_{20}$ to $C_{24}$.

12. A method for obtaining a silicone gel having initial properties of solid (G'>G" and G' is at least 300 Pa) and which reduces to viscosity of 20-1000 cP after fracture, which process comprises mixing 60-95% silicone oil with structuring polymer (b) and optional benefit agent (c) of claim 1.

* * * * *